United States Patent [19]

Reusser et al.

[11] 4,351,980
[45] Sep. 28, 1982

[54] REMOVAL OF OLEFIN FROM ALIPHATIC HYDROCARBON BY TREATMENT WITH ACTIVE SOLID

[75] Inventors: Robert E. Reusser; Elizabeth A. Claytor; Brenton E. Jones, all of Bartlesville, Okla.

[73] Assignee: Phillips Petroleum Company, Bartlesville, Okla.

[21] Appl. No.: 41,454

[22] Filed: May 22, 1979

[51] Int. Cl.³ .............................................. C07C 7/12
[52] U.S. Cl. ............................... 585/820; 252/305; 585/6; 585/722; 585/800
[58] Field of Search ............. 585/720, 820, 721, 722, 585/727, 729, 800, 6; 252/305

[56] References Cited

U.S. PATENT DOCUMENTS

| | | | |
|---|---|---|---|
| 2,564,488 | 8/1951 | Mahan | 585/468 |
| 2,626,967 | 1/1953 | Darragh et al. | 585/451 |
| 2,842,605 | 7/1958 | Appell | 585/721 |
| 2,856,392 | 10/1958 | Tegge et al. | 260/94.8 |
| 2,899,377 | 8/1959 | Findlay | 208/52 |
| 3,394,200 | 7/1968 | Sargent | 585/824 |
| 3,409,691 | 11/1968 | Small | 585/820 |
| 4,028,430 | 6/1977 | Stine et al. | 585/720 |

OTHER PUBLICATIONS

"Ucon Hydrocarbon Propellants", published prior to Aug. 19, 1963 by Union Carbide Chemicals Co., New York, N.Y.

*Primary Examiner*—Curtis R. Davis

[57] ABSTRACT

Hydrocarbon, suitable for use as propellant, is contacted with a solid effective to remove odor-forming impurity therefrom. Hydrocarbons include isobutene-containing stream also containing minor proportions of unsaturated hydrocarbon, e.g. ethylene, propylene, isobutylene, and 2-butenes. Solids include an acid montmorillonite clay, aluminum chloride, $AlCl_3 \cdot HCl$, $AlCl_3 \cdot RCl$, at least one metal of Groups I, II, and III of the periodic table, and supported $H_3PO_4$.

6 Claims, No Drawings

4,351,980

REMOVAL OF OLEFIN FROM ALIPHATIC HYDROCARBON BY TREATMENT WITH ACTIVE SOLID

BRIEF SUMMARY OF THE INVENTION

Low boiling, normally saturated hydrocarbons, useful as propellants, are treated to remove olefin or odor forming impurities therefrom by contacting the same with an active solid, e.g. a hydrocarbon alkylation catalyst such as an acid-treated Montmorillonite clay.

DETAILED DESCRIPTION

This invention relates to the purification of a normally saturated hydrocarbon useful as a propellant. In one of its aspects, it relates to the removal of olefin or odor-forming impurity from a hydrocarbon suitable as a propellant. In a more specific aspect of the invention it relates to the treatment of a saturated hydrocarbon to render the same odor-free and therefore useful as a propellant.

In one of its concepts the invention provides a process for the removal of odor-forming impurities, e.g. olefin from a saturated hydrocarbon otherwise useful as a propellant by contacting the said hydrocarbon with a solid material active to convert and/or to retain within its interstices or pores the odor-forming impurity or material. In another of its concepts, the invention provides a process which comprises contacting a hydrocarbon useful as a propellant with a solid material, normally useful as an alkylation catalyst, to cause removal of odor-forming material, such as olefin, therefrom. In a more specific concept of the invention provides a process for contacting a low-boiling hydrocarbon such as propane, isobutane and/or pentane with a solid, active material suitable to remove impurity or odor-forming material therefrom, e.g., olefin to render the same suitable for use as a propellant, especially in aerosol formulations.

The aerosol industry has for many years successfully employed fluorinated compounds (fluorocarbons) generally having vapor pressures between 15 to 100 psig at 21° C. (70° F.) as propellants for spray-like applications such as for insecticides, paints, deodorants, lotions, cosmetics, hair sprays, and the like. Such fluorocarbons are usually non-flammable, non-toxic and odorless. However, these type propellants have greatly diminished in use because of the environmental impact they allegedly have on the ozone layer of the atmosphere. Because of the similarity in physical properties such as compatibility, vapor pressure and so forth, it has been sought to use low boiling hydrocarbons such as propane, isobutane and pentane to replace the fluorocarbons. A disadvantage of the low boiling hydrocarbons is the small amount of impurities that frequently exist therewith and impart undesirable odors. These odors have been linked to such materials as sulfides, mercaptans and particularly olefins. Removal of these olefin impurities, however, can be a formidable task since quantities as low as 10–50 parts per million (0.001–0.005 wt %) are known to impart some odor to the hydrocarbon.

One of the most popular methods heretofore used for removing olefins from hydrocarbon fractions has been the treatment of the olefin-containing hydrocarbon fraction with strong sulfuric acid. This method has been commonly referred to as acid treating. Although it has been effective in reducing the olefin content of hydrocarbon fractions and has received widespread adoption in industry, it has suffered from a number of disadvantages. Acid treating requires the consumption of large quantities of sulfuric acid and results in the formation of troublesome amounts of acid sludge which present a difficult waste disposal problem. Also, the strong sulfuric acid often causes dimerization of the olefins to other unsaturated olefins that still present a potential odor problem. This results in a need for a distillation step to remove the dimerized material. Another problem, when sulfuric acid is used, is that sulfur dioxide is formed which also must be removed.

Other methods such as those disclosed in U.S. Pat. Nos. 2,636,967; 2,899,377; and 3,394,200 describe procedures for removing odors from hydrocarbons by passing the hydrocarbon fraction over a catalyst bed generally at elevated temperatures and generally with ozone or hydrogen. These methods and other similarly described methods also have disadvantages such as employing dangerous gases or elevated temperatures or loss of catalytic activity, etc.

A more desirable system would be one wherein the hydrocarbon fraction to be purified could be passed over or through a bed of a material active at ambient room temperature with no addition of reactive gases to remove the olefin and wherein the material can be reactivated in-situ for re-use without any significant reduction in catalytic activity.

It is an object of this invention to purify a hydrocarbon. It is another object of this invention to remove an impurity from a hydrocarbon to render said hydrocarbon useful for spray-type application of said hydrocarbon. A further object of the invention is to provide a purified hydrocarbon useful as a propellant in a spray-type application formulation. It is a further object of the invention to provide a process for purification of a low-boiling hydrocarbon to remove odor-forming impurity therefrom to render the same especially applicable for use in an aerosol composition. It is a further object, still, to provide a process for the purification of a hydrocarbon or hydrocarbon fraction by contacting same, without addition of any reactive gas, with a material which will remove odor-forming impurity therefrom at ambient or room temperature.

Other aspects, concepts, objects and the several advantages of the invention are apparent from a study of this disclosure and the appended claims.

According to the present invention there is provided a process for the purification of a hydrocarbon containing odor-forming impurity which comprises contacting said hydrocarbon with a solid material effective to remove said impurity therefrom. More specifically, the process of the invention comprises contacting the hydrocarbon containing the odor-forming impurity e.g., and olefin with a material active to convert and/or to retain said olefin within the interstices or pores of the said material.

Further, according to the invention, materials useful in the process of the invention include solid catalytically active materials such as solid acid-alkylation catalysts known in the art which are active to convert olefins to products which remain in the pores or interstices of the solid. Such solids include acid-treated montmorillonite clays, aluminum chloride, $AlCl_3 \cdot HCl$ or $AlCl_3 \cdot RCl$, where R can be any alkyl or cycloalkyl radical having from 1 to 10 carbon atoms, metals of Group I, II, III of the periodic table, supported $H_3PO_4$, and the like.

The solid materials or catalysts useful in this invention and now preferred can be described as acid-treated diatomaceous earths, minerals or clays, e.g., montmorillonite sub-bentonite clays which have the idealized formula:

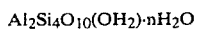

The actual mineral or clay of the given formula has every sixth aluminum ion replaced by a magnesium ion. This produces a crystal lattice with a negative charge which is neutralized by the absorption of metallic cations on the surface. These surface cations are readily removed, and in the process of activation with acid, hydrogen ions are exchanged for the metallic ions, giving, in effect, a solid acid catalyst. The acid-activated material may be designated a magnesium substituted hydrogen montmorillonite. The acid treatment further enhances the catalytic activity of the material by removing inactive impurities and exposing additional contact surface. A catalytic material of this type is sold commercially under the trade name of "Filtrol". A typical mineral analysis of such a catalyst is

| Filtrol Grade - 71 | |
|---|---|
| $SiO_2$ | 71.2% |
| $Al_2O_3$ | 16.5% |
| MgO | 3.2% |
| $Fe_2O_3$ | 3.6% |
| CaO | 2.6% |
| $SO_3$ | 1.3% |
| $K_2O + Na_2O$ | 1.0% |
| $TiO_2$ | 0.6% |
| Acidity, | 5.0–8.0 mg KOH/gm sample |

The montmorillonite clay is acid activated generally by treatment with either sulfuric or hydrochloric acid. The preparation of such acid clays is described by B. A. Stagner, "The Science of Petroleum", Vol. III, page 1699 (1938). U.S. Pat. No. 2,564,488 also describes similar montmorillonite clays as herein described and useful in this invention. Montmorillonite clays having acid numbers from 1–600 preferably 5–400 mg KOH/gram sample are considered to be within the scope of this invention.

The acid-treated montmorillonite clays described herein can be regenerated by any satisfactory means known in the art. Two methods, further described herein, which proved to be satisfactory are, passing a hydrocarbon or an inert gas such as nitrogen through the catalyst bed at elevated temperatures (e.g. 177° C.–204° C.).

Functionally equivalent clays can be used in the process of the invention.

Feedstocks being purified by the process of this invention can be any hydrocarbon generally containing less than 20 wt. percent, preferably less than 5 wt. percent of an olefin or other odor-forming impurity. Of specific importance are hydrocarbon feedstocks potentially useful as aerosols such as propane, 2-methylpropane (referred to herein as isobutane), n-butane, and the pentanes and mixtures of the foregoing. Olefins being removed from these hydrocarbon feedstocks include, but not limited, to such compounds is propylene, isobutylene, n-butenes, pentenes and the like and mixtures thereof. Other impurities like sulfides, mercaptans and other such sulfur-based compounds or oxygenated compounds that contribute to odor are within the scope of this invention.

It will be understood by one skilled in the art that the invention is intended for aerosol applications but other applications requiring an essentially olefin-free product such as polymerization solvents is also within the scope of the invention.

Any type equipment can be used to carry out the current invention, however, a vertical tubular reactor is preferred. The hydrocarbon feedstock flow can be either a down-flow or up-flow as desired. The hydrocarbon feed rate will depend in part on the type of hydrocarbon being treated as well as the amount of odor-forming impurities such as olefins being removed. A typical feed rate is about 5 liquid volumes of hydrocarbon feedstock per volume of montmorillonite clay catalyst used per hour. This is expressed as 5 LHSV, or 5 Liquid Hourly Space Velocity. The same feed rate can also be expressed as 3.86 WHSV or 3.86 Weight Hourly Space Velocity which is 3.86 parts by weight of hydrocarbon feedstock per 1 part by weight of montmorillonite clay catalyst used per hour. Expressing the same rate in the vapor phase, a value of 1230 GHSV (Gas Hourly Space Velocity) would be obtained. The following flow rates are considered within the scope of this invention: LHSV, 0.5–200; WHSV, 0.3–150; GHSV, 100–50,000.

The process described herein can be run preferably at ambient room temperature but it can also be conducted at elevated temperatures if desired. However, temperatures above about 121° C. (250° F.) preferably are not employed for the clays because they begin to significantly lose activity. Any temperature determined by testing to be desirable can be employed. Such temperatures will vary according to the material selected.

The process described herein can be carried either in liquid or vapor phase but liquid phase is preferred. Thus, to conduct the process at liquid phase it may be necessary to operate under a slight pressure particularly with the lower boiling hydrocarbons. For example, when propane is being treated a pressure in the approximate range 130–150 psig may be necessary to maintain a desirable liquid phase. When isobutane is the feedstock a pressure in the approximate range of 40–60 psig may be necessary to maintain a desirable liquid phase.

EXAMPLE I

To a 2.5 cm (1.0 in.) O.D.×53.5 cm (25.0 in) stainless steel tubular reactor was charged 58.3 grams (90 milliliters) of a montmorillonite clay catalyst having an acid number of 5–8 mg KOH/gm sample (Filtrol 71). A slow stream of nitrogen was passed upwardly through the catalyst bed for 2.5 hours at 177° C. (350° F.) to activate the catalyst. The reactor and contents were cooled to room temperature and isobutane containing 282 ppm olefin was passed through the catalyst bed at 6.6 LHSV. A slight nitrogen pressure of 36 psig was maintained. After two hours (13.2 LHSV), the treated hydrocarbon feedstock was analyzed by Gas-Liquid Chromatography (GLC) at 50° C. using 60 cc/min helium flow through 0.635 cm (0.25 inch)×9.135 m (30 foot) column packed with 18% bis [2(2-methyl-ethoxy)ethyl] ether. Table I lists the analysis of isobutane before and after passage through the catalyst bed. The analyses show no significant amounts of olefin present after treatment. The isobutane had a strong odor before treatment but no odor after treatment.

TABLE I

GLC Analysis of Isobutane Before and After Treatment

| | Weight Percent | |
|---|---|---|
| | Before Treatment | After Treatment |
| Ethane | <0.001 | 0.0006 |
| Ethylene | <0.001 | <0.0002 |
| Carbon Dioxide | 0.008 | 0.0003 |
| Propane | 0.173 | 0.154 |
| Propylene | 0.0002 | <0.0002 |
| Isobutane | 96.560 | 96.659 |
| n-Butane | 3.229 | 3.182 |
| Isobutylene or 1-Butene | 0.026 | <0.0003 |
| Trans 2-butene | 0.002 | <0.0003 |
| Cis 2-butene | <0.001 | <0.0003 |
| Isopentane | — | 0.0041 |
| n-Pentane | 0.002 | — |
| Total Olefin | 0.0282 | none |

EXAMPLE II

This example was conducted to illustrate the use of a montmorillonite clay with increased acid content. To a 2.54 cm (1.0 in)×60.96 cm (24 in) Pyrex tube was added 25 milliliters of Mol Sieve (13 X) which was added to remove water. On top of the Mol Sieve was added 50 milliliters (34.3 grams) of the same type of catalyst as used in Example I except more acid was present (e.g. 10 grams $H_2SO_4$/34.3 grams Filtrol 71, tumbled and air dried). After activation and cooling to ambient room temperature isobutane was passed through the column at ambient room temperature and at about 33 psig pressure. The rate of feed was 4.5 LHSV. Analysis of the treated isobutane is shown in Table II.

TABLE II

GLC Analysis of Isobutane

| | Weight Percent | |
|---|---|---|
| | Before Treatment | After Treatment |
| Air | 0.10 | 0.037 |
| Methane | — | 0.109 |
| Ethane | none | 0.047 |
| Ethylene | 0.05 | <0.0005 |
| Carbon Dioxide | <0.001 | 0.018 |
| Propane | 0.54 | 0.508 |
| Propylene | none | <0.001 |
| Isobutane | 94.51 | 94.472 |
| n-Butane | 4.79 | 4.79 |
| Isobutylene or 1-Butene | 0.02 | <0.001 |
| Trans 2-butene | 0.003 | — |
| Cis 2-butene | none | — |
| Isopentane and/or n-Pentane | <0.001 | 0.002 |
| Hexane | — | 0.017 |
| Total Olefins | 0.0230 | none |

A portion of the treated hydrocarbon was evaporated in an Imhoffe tube and the residue analyzed by Mass Spectrometry. The residue was identified as mainly iso-octane and iso-dodecane suggesting that olefin removal occurs via an alkylation mechanism between isobutane and isobutylene or butene.

EXAMPLE III

The procedure described in Example I was repeated with montmorillonite clay catalyst having various acid contents. The hydrocarbon fraction was passed through the catalyst bed until GLC analysis began to indicate the presence of olefin. At this point the run was terminated and the efficiency of the catalyst was measured by comparing either the amount of olefin removed per amount of catalyst used or the amount of feed passed over the catalyst per amount of catalyst used. The data listed in Table III indicate the efficiency of the montmorillonite clay is determined in part by the amount of acid present on the clay, the higher the acid content, the higher the efficiency.

TABLE III

Loading Capacities for Olefins with Different Acidified Montmorillonite Clays

| | Filtrol 71 | Filtrol 24 | Filtrol 71 (29% $H_2SO_4$) |
|---|---|---|---|
| Lbs Olefins Removed per 100 lbs Catalyst Used | 2.6 | 5.54 | 11.24 |
| Gals Feed Per 100 lbs Catalyst Used[a] | 7,500 | 15,716 | 31,886 |
| Volume Feed Per Catalyst Bed Volume | 200 | 553 | 524 |
| Acidity, mg KOH/gm Sample | 5–8 | 12–20 | 330 |
| Heavies wt %[b] | >0.20 | 0.60 | 0.50 |

[a]Calculations are based on isobutane feedstocks containing 0.075 lot % olefins, a feed rate of 5 LHSV, and at room temperature.
[b]Heavies indicated by GLC analysis to be $C_7$ and $C_8$ paraffin hydrocarbons.

EXAMPLE IV

Both Filtrol 71 and Filtrol 24 were regenerated by passing isobutane (0.6 LHSV or ca. 287 ft$^3$/hour/100 pounds of Filtrol 71) or nitrogen (ca. 2200 ft$^3$/100 pounds of Filtrol 71) downflow through the reactor at 177° C. (350° F.) to 204° C. (400° F.). The regeneration off-gas had a very bad mercaptan like odor, especially in the initial stage of regeneration, indicating sulfur and other impurities in the particular isobutane fraction are removed by the Filtrol catalyst. No acidity was detected in the regeneration off-gas, apparently the acid content of the catalysts is not lost on regeneration.

TABLE IV

Regeneration and Calculated Loading Capacity (Isobutane Feedstock)

| | Catalyst Filtrol 71 | Filtrol 71 | Filtrol 24 |
|---|---|---|---|
| Regeneration Agent | $N_2$ | $N_2$ | iso-$C_4$ |
| Temp °C. | 177 | 177 | 177 |
| Original Loading | | | |
| Lbs Olefin/100 lbs Cat. | 2.91 | 2.46 | 3.56 |
| Gal/100 lbs Cat. | 8,255 | 6,978 | 10,100 |
| Loading After Regeneration | | | |
| Lbs Olefin/100 lbs Cat. | 2.61 | 2.13 | 3.53 |
| Gal/[a] 100 lbs Cat. | 7,404 | 6,042 | 10,000 |

[a]Gallons of feedstocks treated are based on it containing 0.075 wt. % olefins, at a 5 LHSV feed rate, and percolating at room temperature.

The data listed in Table IV indicate the Filtrol catalyst can be successfully regenerated to maintain the same degree of efficiency of the catalyst.

For best results, whenever moisture content of the hydrocarbon being purified will interfere with the removal of the odor-forming impurity, it is now preferred to remove moisture or water from the hydrocarbon. Such removal can be practiced according to available methods.

Reasonable variation and modification are possible within the scope of the foregoing disclosure and the appended claims to the invention the essence of which is that odor-forming impurity, e.g. olefin, is removed from a hydrocarbon otherwise suitable for use as a propellant by contacting a said hydrocarbon, preferably after removal of any undesired amount of moisture, with a solid acid-alkylation effective to convert and/or to take within its interstices or pores the odor-forming impurity.

We claim:

1. A process for the removal of a small amount of an odor-forming impurity of the order of a few parts per million from a low boiling isoparaffin hydrocarbon aerosol propellant for spray-type application which comprises contacting said hydrocarbon with a solid-acid treated montmorillonite clay catalyst effective to remove said odor-forming impurity.

2. A process according to claim 1 wherein the low boiling isoparaffin hydrocarbon is isobutane.

3. A process according to claim 1 wherein said catalyst is a magnesium-substituted hydrogen montmorillonite having the approximate analysis

| | |
|---|---|
| $SiO_2$ | 71.2% |
| $Al_2O_3$ | 16.5% |
| MgO | 3.2% |
| $Fe_2O_3$ | 3.6% |
| CaO | 2.6% |
| $SO_3$ | 1.3% |
| $K_2O + Na_2O$ | 1.0% |
| $TiO_2$ | 0.6% |
| Acidity | 5.0–8.0 mg KOH/gm sample |

4. A process according to claim 3 wherein the acidity of the clay is in the approximate range of from about 5 to about 8 milligrams KOH/gm.

5. A process according to claim 1 wherein the hydrocarbon is a low-boiling hydrocarbon containing a minor amount of at least one of the following: olefin, sulfide, mercaptan and oxygenated compounds.

6. A process according to claim 1 wherein the odor-forming impurity is at least one of the following: ethylene, propylene, isobutylene, n-butenes, and pentenes.

* * * * *